(12) United States Patent
Brock

(10) Patent No.: US 6,297,020 B1
(45) Date of Patent: Oct. 2, 2001

(54) DEVICE FOR CARRYING OUT LATERAL-FLOW ASSAYS INVOLVING MORE THAN ONE ANALYTE

(75) Inventor: David A. Brock, Elkhart, IN (US)

(73) Assignee: Bayer Corporation, Elkhart, IN (US)

( * ) Notice: Subject to any disclaimer, the term of this patent is extended or adjusted under 35 U.S.C. 154(b) by 0 days.

(21) Appl. No.: 09/259,353

(22) Filed: Mar. 1, 1999

(51) Int. Cl.$^7$ .................................................. G01N 33/543
(52) U.S. Cl. ................................ 435/7.1; 422/55; 422/56; 422/57; 422/58; 422/61; 435/287.1; 435/287.2; 435/287.7; 435/287.9; 435/805; 435/810; 435/970; 435/973; 436/169; 436/514; 436/518; 436/530; 436/535; 436/805; 436/810; 436/815
(58) Field of Search ................................ 422/55–58, 61; 435/287.1, 287.2, 287.7, 287.9, 805, 810, 970, 973, 7.1; 436/169, 514, 518, 530, 535, 805, 810, 815

(56) References Cited

U.S. PATENT DOCUMENTS

| 4,703,017 | 10/1987 | Campbell et al. | 436/501 |
| 5,384,264 | * 1/1995 | Chen et al. | 436/525 |
| 5,739,041 | 4/1998 | Nazareth et al. | 436/518 |

FOREIGN PATENT DOCUMENTS

| 0 462 376 | 12/1991 | (EP) . | |
| 0 291 194 | 12/1994 | (EP) . | |
| 88/08534 | * 11/1988 | (WO) | 435/970 |
| WO 96/38720 | 12/1996 | (WO) . | |

* cited by examiner

Primary Examiner—Christopher L. Chin
(74) Attorney, Agent, or Firm—Jerome L. Jeffres

(57) ABSTRACT

Disclosed is an improvement to a dry assay device for determining the concentration of a first analyte in a sample of body fluid and a second analyte in the same sample of body fluid. The device involves the use of a strip of an absorbent material through which the sample of body fluid flows and wherein the first analyte is determined calorimetrically in a first region of the strip and the second analyte is determined by an immunoassay which takes place in a second region of the strip located downstream from the first region. The improvement involves placing the strip in a hollow casing having a top and a bottom and which is so constructed that when the top and bottom of the casing are mated there is formed a U shaped, body fluid impervious barrier around the first region of the strip to prevent the sample of body fluid from flowing in any direction other than in the direction of the second region of the strip.

11 Claims, 1 Drawing Sheet

DEVICE FOR CARRYING OUT LATERAL-FLOW ASSAYS INVOLVING MORE THAN ONE ANALYTE

BACKGROUND OF THE INVENTION

Immunochromatographic strip formats have become increasingly popular for qualitative and semiquantitative assays which use visual detection schemes. This type of assay involves the application of a liquid test sample suspected of containing the analyte to be detected to an application zone of an immunochromatographic test strip. The strip is comprised of a matrix material through which the test fluid and analyte suspended or dissolved therein can flow by capillarity from the application zone to a capture zone where a detectable signal, or the absence of such, reveals the presence of the analyte. Typically, the strip will include means for immunospecifically binding the analyte to be detected with its specific binding partner which bears the detectable label. In one such scheme, the strip contains an enzyme labeled, mobile binding partner for the analyte which is in a zone downstream from the sample application zone. If analyte is present in the test sample, it will combine with its labeled binding partner to form a complex which will flow along the strip to a detection zone which contains a substrate for the enzyme label which is capable of providing a colored response in the presence of the enzyme. The strip may contain a zone in which analyte is immobilized, so that labeled binding partner which does not combine with analyte, due to the absence of analyte in the sample, will be captured and thereby inhibited from reaching the detection zone. There have been published various modifications of this technique, all of which involve some competitive specific binding system in which the presence or absence of analyte in the test sample is determined by the detection or lack thereof of labeled binding partner in the capture zone.

An alternative to the above described immunometric assay which detects the free labeled antibody is the so called sandwich format in which the capture zone contains immobilized antibodies against an epitope of the analyte which is different than the epitope to which the labeled antibody is specific. In this format, there is formed a sandwich of the analyte between the immobilized and labeled antibodies and it is therefore an immunometric assay which detects the bound labeled antibody species.

Not all of the schemes for immunochromatography rely on an enzyme labeled binding partner/enzyme substrate for providing the signal for detection of the analyte. In U.S. Pat. No. 4,806,311 there is disclosed a multizone test device for the specific binding assay determination of an analyte and an immobilized binding partner therefore together with a capture zone for receiving labeled reagent which migrates thereto from the reagent zone. The capture zone contains an immobilized form of a binding substance for the labeled reagent. The labeled reagent bears a chemical group having a detectable physical property which is detectable on the basis of such physical property, so that it does not require a chemical reaction with another substance in order to be detected. Exemplary of such groups are colored species of fluorescers, phosphorescent molecules, radioisotopes and electroactive moieties.

U.S. Pat. No. 4,703,017 describes the use of visible particulate labels for the receptor. Various particulate labels such as gold sol particles and visible dye containing liposomes are mentioned. In WO-96/34271 there is disclosed a device for determining a target analyte and creatinine in a fluid test sample which device has an assay strip for the detection of creatinine and a second assay strip for the detection of the target analyte. The creatine concentration can be determined calorimetrically or by the specific capture of labeled creatinine binding partners. The concentration of the target analyte is corrected based on the sample's creatinine concentration which correction can either be done manually or by means of a properly programmed reflectance analyzer.

EP 0 462 376 discloses an immunochromatographic procedure in which signal at the capture site and the conjugate recovery site of the strip are detected and the analyte concentration is determined by the intensity of the signal at the capture site relative to the signal at the conjugate recovery site.

Immunochromatographic strip formats provide a viable system for the determination of various analytes (whether they be antigens or antibodies) but suffer from the limitation that they yield results which are at best semi-quantitative when, for some analytes, more precise, quantitative results are required.

In WO-96/38720 there is disclosed a chromatographic assay device for the detection and/or determination of an analyte while giving a positive indication that flow has occurred properly through the device. The device comprises an opposable component including a sample preparation zone and an absorber together with a second opposable component including a first chromatographic medium with capture/detection zones and a second chromatographic medium with a comparison zone and a comparison label zone. The opposable components are typically joined by a hinge so that the opposable components can be folded over upon each other to form a unitary cassette in which the chromatographic medium is encased.

SUMMARY OF THE INVENTION

The present invention is an improvement to a dry assay device for determining the concentration of a first analyte in a sample of body fluid and a second analyte in the same sample of body fluid. The first analyte is determined calorimetrically by the color change in a first zone of a strip of absorbent material through which the body fluid sample flows and the concentration of the second analyte is determined by an immunoassay in which the body fluid and analyte flow through a second zone of the strip which is in fluid communication with the first zone and analyte in the body fluid is immobilized in one of these zones by interaction between the analyte and an immobilized specific binding partner to provide a detectable signal. The improvement comprises placing the strip of absorbent material in a hollow casing having a top and a bottom and which is constructed in a manner such that when the top and bottom portions of the casing are mated there is formed a U shaped body fluid impervious barrier around the first zone of the strip thereby preventing the sample of body fluid from flowing in any direction other than towards the second zone of the strip.

DESCRIPTION OF THE INVENTION

Figure 1:
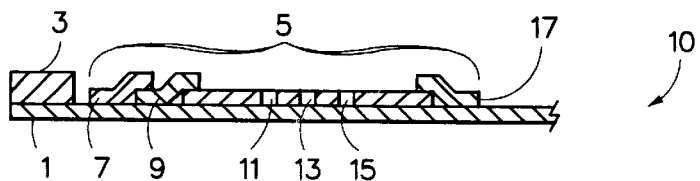
FIG. 1 represents the strip component of the device of the present invention.

Referring to FIG. 1, the strip 10 has a solid support 1 which supports a chemistry reagent pad 3 in which there are absorbed reagents for the calorimetric determination of a first analyte. Downstream from the chemistry reagent pad is the region 5 in which the immunoassay is carried out. This region contains wicking pad 7 and reagent zone 9 which contains labeled antibodies specific for the analyte whose concentration is being determined. These portions of the strip are depicted as overlapping the next adjacent portion of the strip. This is an optional configuration which provides for greater contact area between the zones thus facilitating fluid flow through the strip. This is not essential since simple connectors such as head to tail contact are sufficient when the test fluid is one which can flow easily through the strip. The label is preferably a visible particulate label such as gold sol, however, an enzymatic label could be used provided the capture zones 11 and (optional second capture zone 13) contain an appropriate substrate for the enzyme. Capture zones 11 and 13 contain either immobilized analyte or an immobilized antibody specific for an epitope of the analyte distinct from that to which the labeled antibody is specific. In the first embodiment there takes place a competitive reaction in which analyte in the test fluid and that which is immobilized in the capture zone(s) compete for labeled antibody. In this format, the strength of the signal from the capture zone will be inversely proportional to the concentration of analyte in the test fluid. In the sandwich format, there will be immobilized in the capture zone(s) antibodies specific to a second epitope on the analyte which is distinct from that to which the labeled antibody is specific. In this format the strength of the signal from the capture zone(s) will be directly proportional to the concentration of analyte in the test sample. The strip may also contain a control region 15 which is typically a positive control in which labeled antibody is captured by a specific capture means such as immobilized anti-mouse IgG. The strip will also normally have an absorbent pad 17 which absorbs test fluid and thereby encourages its flow through the strip.

Figure 2:
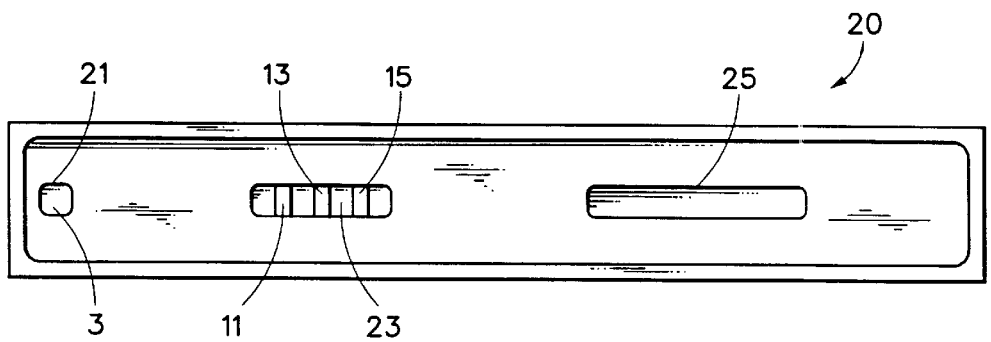
FIG. 2 is a top view of the casing portion of the present device.

FIG. 2 is a top view of the casing 20 which contains the strip of FIG. 1. The casing has an application port 21 through which the test sample is applied and any color change in the chemistry reagent pad 3 can be observed. There is a second viewing port 23 through which the capture band(s) 11 and 13 as well as the optional collection band are viewed.

The top of the casing may be provided with a second viewing port 25 through which other colored indications may be viewed. For example, the strip may contain colored bands which are coded to identify the assay or a thermochromic liquid crystal which can be used to measure the temperature of the strip, so that corrections based on temperature related variables can be made.

Figure 3:
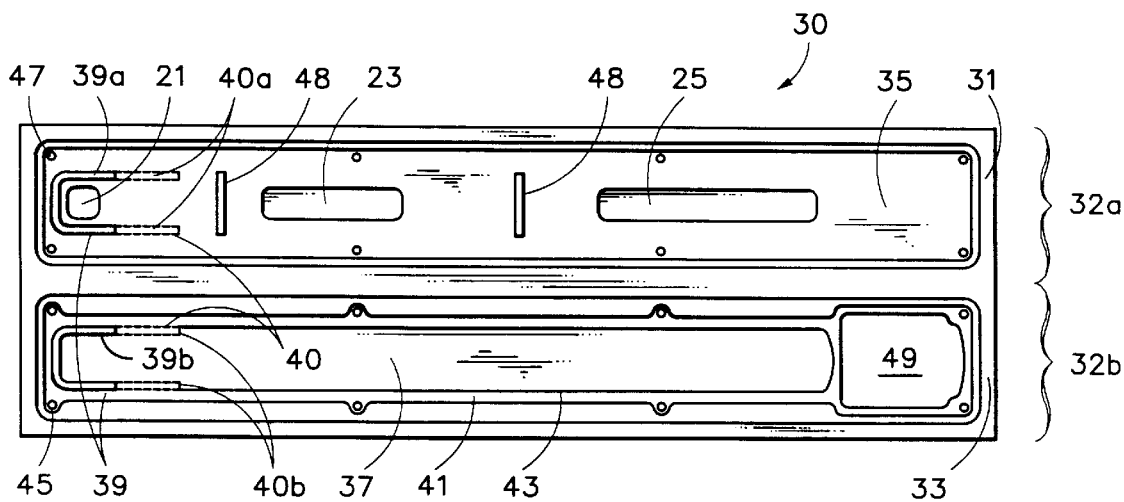
FIG. 3 depicts the top and bottom of the casing segment of the device showing these segments before they are folded over each other and snapped into place to house the strip.

The directional flow features of the present invention are illustrated by FIG. 3, in which the casing 30 is shown with its top 31 and bottom 33 in the open position. The top of the casing has an indentation 35 and the bottom of the casing has an indentation 37 which form a hollow chamber of sufficient size to hold the strip when the top and bottom are mated after placing the strip in the indentation 37 in the casing's bottom portion. The casing is designed to hold the strip so that the chemistry reagent pad 3 is aligned with the sample application port and surrounded on three sides by the U shaped barrier 39 which, when the top and bottom of the casing are mated, forms a fluid impervious barrier around this region of the strip. The U shaped barrier precursors 39a and 39b which form the barrier 39 by contact between barrier precursors 39a on the top portion of the casing and 39b on the bottom portion when the top and bottom are mated need not be equally divided between the top and bottom of the casing. The only requirement is that precursor 39a on the casing top and 39b on its bottom join snugly when the casing top and bottom are mated to thereby form a U shaped dam that prevents the fluid sample from flowing in any direction other than towards the second and subsequent zone(s) of the strip in which the immunoassay is carried out.

While barrier precursors 39a and 39b will both normally project above the plane of the casing's top and bottom respectively, this is not critical since barrier precursor 39a or 39b can be in the same plane as the casing top or bottom with all of the projecting portion necessary to form barrier 39 being on the other surface. As represented by the phantom portions of FIG. 3, 40a and 40b, the barrier can extend further down the strip to extend beyond the wicking portion of the immunochromatography portion. This will provide additional reliability by insuring that fluid sample entering the sample port 21 will fully inoculate the immunoassay portion of the strip.

In another embodiment of the invention, barrier precursor 39a is slightly narrower than chemistry reagent pad 3 and precursor 39b is molded to have a height from the casing bottom's surface less than the thickness of the pad, so that when the casing's top and bottom are mated the chemistry reagent pad is squeezed between barrier precursors 39a and 39b to reduce the chance that a capillary gap will form between the walls of the casing and the reagent pad. If such a gap were to form, the fluid sample introduced through the entry port would travel into the gap and not toward the wick of the immunoassay portion of the strip. The bottom portion of the casing can be equipped with troughs 41 on one or both sides of the area in which the strip rests to serve as drainage fields which serve to remove any excess fluid sample applied to the sample port. The casing bottom can be advantageously equipped with a ridge 43 which is in the outline of the strip and serves to ensure proper placement in the casing. This ridge should be fairly shallow, so that excess test fluid can flow over it into drainage troughs 41. The casing top and bottom can also be equipped with a series of pins 45 which lock up with holes 47 when the top and bottom of the casing are mated to hold them snugly together. The cassette top may be equipped with pressure bars 48 which are designed to hold the strip firmly against the bottom of the casing when the casing top and bottom are mated to prevent fluid sample from flowing under the strip. Depression 49 in the bottom of the strip is optionally present to hold a desiccant bead.

The strip can be prepared from any matrix material through which the test fluid carrying the analyte, labeled binder and/or labeled binder-analyte conjugate contained therein can flow by capillarity and can be of a material which is capable of supporting non-bibulous lateral flow as described in U.S. Pat. No. 4,943,522 as liquid flow in which all of the dissolved or dispersed components of the liquid are carried through the matrix at substantially equal rates and with relatively unimpaired flow as contrasted to preferential retention of one or more components as would be the case if the matrix material were capable of absorbing or imbibing one or more of the components. An example of such matrix material is the high density or ultra high molecular weight polyethylene sheet material from Porex Technologies. Equally suitable for use as the matrix from which the chromatographic strip can be fabricated are bibulous materials such as paper, nitrocellulose and nylon.

Various immunochromatographic strip formats are suitable for those portions of the strip which are downstream from the pad containing the colorimetric reagents. The type of chemistry reagent pad may vary depending on the analyte of interest relative to the immunoassay. The reagent pad generally consists of an absorbent material such as a paper or membrane that has been impregnated with a respective reagent associated with a particular test to be performed. With urinalysis testing, this reagent pad may be, for example, a test for creatinine, a test for leukocytes, a test of pH or a test of blood. An adhesive backing is placed on the dried, impregnated paper and cut into a ribbon of a desired width. The ribbon is adhered to a support at a location that would place the reagent under the sample port of the casing. Once all the immunoassay components are in place on the support, the support is cut to the dimensions that are needed for the strip to lie in the cavity of the casing bottom. When the reagent pad encounters the sample, the pad changes color over time and the reflectance of the color, which is proportional to the amount of analyte present in the sample, is measured. A particularly suitable format is that which is disclosed in U.S. Pat. No. 4,446,232 in which there is described a device for the determination of the presence of antigens, which device comprises a strip of matrix material having a first zone in which there are provided immobilized analyte and enzyme linked antibodies specific to the analyte to be determined. The labeled antibodies can flow to a second zone when reacted with analyte introduced into the first zone via the test sample but will not so flow in the absence of analyte in the test fluid since the labeled antibodies will be bound in the first region by interaction with the immobilized analyte. The analyte is typically an antigen, although the format can be designed to detect the presence of antibodies as analyte. An alternative to this format is a sandwich format in which the labeled antibody is specific for one epitope of the analyte and there is immobilized in the capture zone a second antibody which is specific to a second epitope of the analyte so that there is formed in the capture zone an antibody-analyte-labeled antibody sandwich in the presence of analyte in the fluid test sample. As an alternative to the use of an enzyme label, the antibodies used in the device can be labeled with a visible particulate label such as colored latex or metal sol. This is the preferred form of labeling, although any physically detectable signal generator may be used as the label.

In operation, the device is used by pipetting the fluid sample, which is typically urine, through the sample application port 21. This will result in wetting of the pad containing the calorimetric reagents and a reaction between the first (reference) analyte and the calorimetric reagents for the determination of this analyte. Such reagents can comprise an oxidase enzyme, a pseudoperoxidase and an oxidizable dye so that interaction between the reagent system and analyte in the test fluid will produce a colored response upon oxidation of the dye. A common reference analyte in urinalysis is creatinine, the end metabolite when creatine becomes creatine phosphate which is used as an energy source for muscle contraction. The creatinine produced is filtered by the kidney glomeruli and then excreted into the urine without reabsorption. In order to increase the sensitivity of urinary assays and minimize the problem of high urine flow rates which result in urine dilution, analyte/creatinine ratios are used in urine analyte assays to normalize the urine concentration. Common creatinine assays include the alkaline Jaffe and Benedict-Behre methods which are run at a high pH, typically in the range of from 11.5 to 12.5. More recently, there has been developed a creatinine assay in which the urine sample is contacted with cupric ions in the presence of citrate, a hydroperoxide and an oxidizable dye which provide a colored response in the presence of oxygen free radicals and a pseudoperoxide. This method is more fully described in U.S. Pat. No. 5,374,561 incorporated herein by reference. Referring to FIG. 1, the present invention can be used for the determination of protein in urine by incorporating the creatinine reagent into colorimetric chemistry reagent pad 3. Upon application of the urine test sample the creatinine concentration can be determined calorimetrically such as by the use of a reflectance spectrometer. The urine sample will continue to flow down the strip of absorbant material, through the wicking pad 7 and reagent zone 9. The U shaped barrier, which surrounds at least the chemistry reagent pad 3, prevents the test sample from flowing in any direction other than downstream from this pad thereby improving the accuracy of the assay which is carried out using the test strip. Extending the legs of the U shaped barrier further down the strip, to cause them to be co-extensive with the wicking pad 9 or even further down the strip will further enhance the device's accuracy. After flowing through the wicking pad 9, and into reagent zone 9, the test sample contacts the labeled antibodies which flow along with the fluid sample towards the capture zone 11 where the labeled antibodies are captured either by interaction with immobilized analyte or interaction between analyte in the fluid test sample, the labeled antibodies specific thereto and antibodies immobilized in the capture zone which are specific to another epitope on the analyte to form a sandwich. Regardless of how the labeled antibodies are captured in the capture zone, there will be generated two signals in the strip; the first by the interaction of creatinine in the urine test sample with the creatinine reagent in reagent pad 3 and the second from the labeled antibody in capture zone 11. These signals can be read by a properly programmed reflectance spectrometer and rationalized to give a result which is the urine sample's protein concentration which has been corrected for the urine's flow rate by using the creatinine concentration.

The reference analyte is not limited to creatinine since any reference analyte whose concentration in a sample of body fluid is clinically related to the concentration of the target analyte can be measured by its reaction with the reagent pad 3. Thus, for example, the body fluid tested can be whole blood, the target analyte can be $HbA_{1c}$ and the second analyte can be total hemoglobin since the apparent concentration of $HbA_{1c}$ can be adjusted to the whole blood's total hemoglobin concentration to factor out bias in the $HbA_{1c}$ assay. Inulin, administered intravenously, is, like creatinine, an indicator of renal flow. Clinically significant results can be obtained by determining the ratio of these pairs of analytes in the sample of body fluid.

Many clinically significant target analytes are present in urine and as determinable by means of the present invention. Among these analytes are deoxypyridinoline, human serum albumin, drugs of abuse such as amphetamines/barbiturates/cocaine, clinically important protein markers such as prostate specific antigen, kidney disease proteins such as lactate dehydrogenate, N-acetyl-B-D-glucosamine, pregnancy or fertility associated hormones such as human chorionic gonadotropin and markers of urinary tract infection.

While the means for detecting the signal from the developed strip of the device of the present invention will depend on the detectable label attached to the labeled binding partner, the use of a reflectance spectrometer is typical when the label's detectable physical property is the reflectance of light at a predetermined wavelength. In a preferred method of using the device there is provided a reflectance meter with means for moving the strip or the meter's detector element relative to each other such as by use of a specimen table for the strip which can be moved laterally under the readhead of the detector. The reflectance from the chemical reagent pad can be read to obtain the concentration of this reference analyte in the fluid sample and then the device can be shifted on the specimen table for reading the concentration of the target analyte to provide raw data which the reflectance spectrometer's pre-programmed software can use to provide the corrected concentration of the target analyte.

The method of practicing the present invention is more fully illustrated by the following example:

EXAMPLE I

A study was carried out testing the fluid sample flow characteristics within two different casing types; one with (1) and one without (2) the "U" shaped barrier. The strip design used in model 1 was constructed to incorporate the wicking pad of the immunoassay portion to lay beneath the creatinine reagent and was referred to as the underpad format. The model 2 casing had both the underpad format and a strip format wherein the wicking pad for the immunoassay came within 0.0245" of the creatinine reagent pad. The creatinine reagent pad demonstrated in this example was paired with a deoxypyridinoline (Dpd) immunoassay. The creatinine reagent pad was made of an absorbent paper impregnated with reagents to provide a test based on the peroxidase like activity of a copper creatinine complex which catalyzes the reaction of diisopropylbenzene dihydroperoxide and 3,3',5,5' tetramethylbenzidine to provide a color change in the presence of creatinine.

The study was analyzed for two effects, i.e. the number of failures when the Dpd immunoassay was not inoculated after adding the sample and for which casing format provided better performance (% CV) for the Dpd capture bands using the reflectance value at 565 nm. A third strip format ("dip and read") was used as a control. A buffer solution containing Dpd and creatinine concentrations within the intended range was used as control. Testing was done using 15 replicates for each format, except for model 2 (underpad) which used only 7 replicates. The results of the study were that (1) there were no failures of inoculation of the Dpd immunoassay for either casing model, although in a previous study there was noted a failure of inoculation of the model 1 cassettes; (2) the model 2 casing provided better performance in terms of lower % CV for the Dpd immunoassay as shown in the following table.

| | % reflectance at 565 nm | | |
|---|---|---|---|
| Format | mean | SD | % CV |
| Model 1 cassette (underpad) | 50.5 | 2.3 | 4.5 |
| Model 2 cassette (underpad) | 49.4 | 1.7 | 3.5 |
| Model 2 cassette (0.025" gap) | 47.7 | 1.1 | 2.4 |
| "dip and read" strip | 48.3 | 1.3 | 2.8 |

What is claimed is:

1. In a dry assay device for determining the concentration of a first analyte in a sample of a body fluid and a second analyte in the same sample of body fluid in which the first analyte is determined colorimetrically by the color change in a first discrete zone of a strip of absorbant material through which the body fluid sample can flow and the concentration of the second analyte is determined by an immunoassay in which the body fluid and analyte flow through a second zone of the strip which is in fluid communication with the first zone and analyte labeled specific binding partner conjugate in the body fluid is immobilized in one of these zones by interaction between the analyte or the specific binding partner and an immobilized binder in a separate zone of the strip to provide a detectable signal, the improvement which comprises placing the strip in a hollow casing constructed of a body fluid sample impervious solid material having a top and a bottom which when mated provide a hollow chamber suitable for holding the strip, which chamber is in fluid communication with the exterior of the casing through an opening in the top of the casing which is aligned with the first discrete zone of the strip and when the top and bottom of the casing are mated there is formed a U shaped, body fluid sample impervious barrier around the first discrete zone of the strip and not extending along the entire length of the strip which prevents test fluid from flowing in any direction other than in the direction of the second zone and any subsequent zone(s) of the strip.

2. The device of claim 1 wherein the concentration of the first analyte is clinically related to that of the second analyte.

3. The device of claim 1 wherein a portion of the U shaped barrier is fixed to the top of the casing and a portion is affixed to the bottom of the casing.

4. The device of claim 1 wherein the U shaped barrier extends downward along the strip beyond the end of the first discrete zone.

5. The device of claim 1 wherein the second zone of the strip is divided into sub zones one of which is an absorbant wicking pad and the U shaped barrier extends downward along the strip to the end of this sub zone.

6. The device of claim 1 wherein the top and bottom portion are constructed so that a press fit secures them together to form the casing having the hollow chamber.

7. The device of claim 1 wherein the casing is made of plastic.

8. The device of claim 7 wherein the plastic is polystyrene, an acrylic polymer or a polyurethane.

9. The device of claim 1 wherein the bottom portion of the casing is equipped with a ridge in the shape of the strip to ensure proper placement of the strip in the casing.

10. The device of claim 1 wherein the body fluid is urine.

11. The device of claim 10 wherein the first analyte is creatinine and the second analyte is deoxypyridinoline.

* * * * *